United States Patent [19]

Gagnebin et al.

[11] Patent Number: 5,083,908
[45] Date of Patent: Jan. 28, 1992

[54] MINIATURE PERISTALTIC PUMP

[75] Inventors: Eric Gagnebin, Marin; Clément Meyrat, Le Landeron, both of Switzerland; Antoine Dubois, Villers-le-Lac, France

[73] Assignee: Asulab S.A., Bienne, Switzerland

[21] Appl. No.: 497,697

[22] Filed: Mar. 23, 1990

[30] Foreign Application Priority Data

Mar. 24, 1989 [CH] Switzerland ............ 8904044

[51] Int. Cl.⁵ ............................................. F04B 43/12
[52] U.S. Cl. ................................. 417/477; 604/153
[58] Field of Search .................. 417/475, 477, 435; 604/153

[56] References Cited

U.S. PATENT DOCUMENTS

| | | | |
|---|---|---|---|
| 3,737,251 | 6/1973 | Berman et al. | 417/475 X |
| 3,742,697 | 7/1973 | Hama | 58/23A |
| 4,573,887 | 3/1986 | Smith | 417/477 |
| 4,692,147 | 9/1987 | Duggan | 604/93 |
| 4,813,855 | 3/1989 | Leveen et al. | 417/477 |
| 4,834,630 | 5/1989 | Godwin | 417/475 |
| 4,968,229 | 11/1990 | Nevder | 417/477 |

FOREIGN PATENT DOCUMENTS

| | | |
|---|---|---|
| 2166467 | 8/1973 | France . |
| 2595765 | 9/1987 | France ................ 417/477 |
| 2138511 | 10/1984 | United Kingdom . |

OTHER PUBLICATIONS

Life Support Systems, vol. 1, No. 1, Jan./Mar. 1983, pp. 23-28, Prestele et al.

*Primary Examiner*—Richard A. Bertsch
*Assistant Examiner*—David L. Cavanaugh
*Attorney, Agent, or Firm*—Griffin Branigan & Butler

[57] ABSTRACT

The miniature peristaltic pump (1) of this invention includes a pump module (2) comprising a gear (11) arranged to drive a rotor bearing rollers, said rollers crushing locally at least one tube into which a medicinal preparation may be sucked in at the input (13) and expelled at the output (14) thereof. The gear (11) meshes with a pinion (12) forming part of a motor module (3) adapted to be mounted with or dismounted from the pump module. The motor module comprises a timepiece movement of the type currently employed in a wrist watch, such movement including a stepping motor, an integrated circuit, a quartz resonator and down gearing by means of toothed wheels. An energy cell renders the pump self contained. The pump is intended to be carried on the human body and thus renders unnecessary that the patient recline on a bed.

10 Claims, 5 Drawing Sheets

MINIATURE PERISTALTIC PUMP

This invention concerns a miniature peristaltic pump especially adapted to be carried on the human body for slow and continuous injection of medicinal preparations in the aqueous state, including a pump having a rotor borne on a shaft around which are evenly distributed rollers given a revolving movement rolling along at least one flexible tube so as to compress it against at least one backing which surrounds said tube over a predetermined length of arc so as to permit the sucking in and the expelling of said medicinal preparation, said shaft being provided with a coupling element, a stepping motor driving a down gearing chain bearing at its end a power take-off, a control circuit for providing the motor with energizing pulses coming from a time base followed by a frequency divider and a power cell.

BACKGROUND OF THE INVENTION

Peristaltic pumps which permit precise dosage of the liquid to be administered, for instance to a patient in the form of a perfusion, are known as much in research applications as in therapeutic employment. One will find in patent documents U.S. Application No. 4 715 786 and WO 88/10 372 descriptions of peristaltic pumps, the principle of which is well known and which generally consists in employing an elastically deformable tube to be locally crushed against a sump by means of a rotor equipped with revolving rollers and thus sucking in, then expelling the liquid contained in the tube coming from a reservoir. By varying the speed of rotation of the rotor, one may modify the pump discharge. Such discharge may even be programmed over a time period, this as a function of the requirements established by the illness to be cared for or by the experiment which is to be carried out.

Peristaltic pumps equipped with a single tube or flexible pipe exhibit the shortcoming of discharging the liquid which they are intended to transport in a sinusoidal manner, thus irregularly. In order to overcome this problem, there has been proposed the simultaneous employment of two coupled pumps provided with two flexible pipes placed in parallel on which act respectively two rotors provided with rollers. A first pump of this nature is described in the patent document WO 82/04 291 where the rollers on one rotor are angularly offset relative to the rollers of the neighbouring rotor. A second such pump is described in the patent document GB 1 595 901 where the two rotors exhibit coaxial rollers two by two and where the flexible pipes are offset relative to one another in a manner such that when a roller of the first rotor crushes the first pipe in the middle of its active length, the second pipe is simultaneously crushed by two rollers of the second rotor at the beginning and at the end of its active length. Whatever be the solution chosen, it will be understood that, as described, one obtains a much more regular discharge since the sinusoidal discharges given by the two pumps taken independently are offset in time and compensate one another so as to obtain a substantially constant discharge.

The document Life Support Systems (1983), 1, 23-28 describes a peristaltic pump which is implantable into the body. From this particularity there ensues the fact that all components of the pump are hermetically encapsulated in a case of titanium. The pump reservoir is filled in a percutaneous manner by means of a syringe. The driving motor of the pump is of the stepping type. It is energized by a time base followed by a frequency divider and a battery. The pump is externally programmable by means of a control apparatus coupled by magnetic induction to the pump.

The patent document FR-A-2 479 692 (=U.S. Application No. 4 692 147) also describes a peristaltic pump which is implantable into the body, the generic characteristics of which respond in all points to those described in the preceding paragraph.

The peristaltic pumps known from the documents cited hereinabove exhibit construction principles which generally are closely related to the definition given in the first paragraph of this description and which partially describes the pump according to this invention. At the same time, none of the cited pumps and generally no other pump currently known in practice is susceptible to be portable, for instance on the human body for the slow and continuous injection of medicinal preparations. The prior art pumps are heavy and voluminous and if they are employed for purposes of perfusion, are arranged on a table in proximity to a patient prone on a bed.

In contrast to this, the pump according to this invention is portable next to the body, this enabling a patient to move around and even to attend to his usual occupations. To attain this purpose, the pump of the invention is a miniature pump taking up little space. Another aim of the pump according to the invention is that of being inexpensive to such a point that it may be thrown away following use, thus avoiding all risk of contamination. Yet another purpose of the pump according to the invention is that of having two modules, a pump module and a motor module which are separable by the practitioner himself who could be either a medical doctor or a nurse, this in order to enable sterilization of the pump module and/or choice of a motor module adapted to the illness to be cared for.

SUMMARY OF THE INVENTION

In order to achieve these ends and the advantages which they bring, the portable miniature peristaltic pump of the invention is characterized in that it includes a first or pump module and a second, or motor module, said modules being adapted to be connected to or disconnected from one another, the pump module comprising the pump itself provided with its coupling element and the motor module comprising the stepping motor, the down gearing chain provided with its power take-off, the control circuit, the time base, the frequency divider and the power cell, said coupling element being engaged with said power take-off when said modules are assembled.

The invention will be understood with the aid of the description to follow and which gives by way of example and with the help of the accompanying drawings a practical embodiment of the invention.

DESCRIPTION OF THE PREFERRED EMBODIMENT

Figure 1:
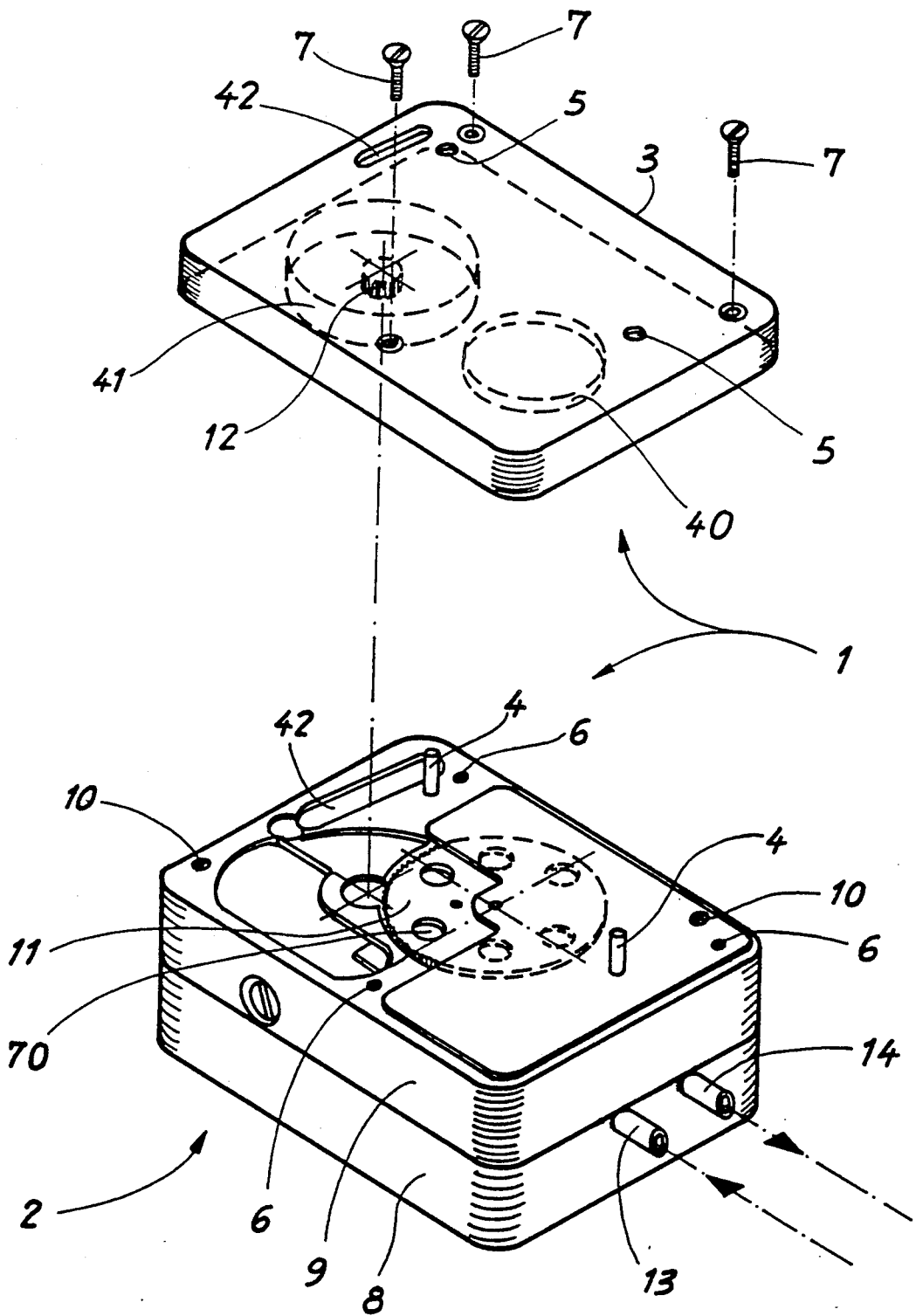
FIG. 1 is a perspective view of the pump according to the invention, such view showing at the bottom of the figure a pump module and above a motor module, such modules being disconnected.

FIG. 1 shows a peristaltic pump 1 in accordance with a preferred embodiment of the invention. The pump includes a pump module 2 and a motor module 3. As may be seen on the figure, modules 2 and 3 are adapted to be connected to and disconnected from one another. For this the pump module bears centering studs 4 which are introduced into centering holes 5 pierced in the motor module when the two modules are assembled. The pump module bears threadings 6 which receive screws 7 thanks to which the modules may be fastened to one another. As further shown on FIG. 1, the pump module 2 is formed in two parts comprising a pump body 8 and a cover 9. The body of the pump and the cover are held together by means of screws 10. The pump module 2 is provided with a coupling element, in this case a gear 11, by which the pump may be driven and the motor module 3 includes a power take-off, in this case a pinion 12, adapted to drive the coupling element 11 when the two modules are assembled. The pump module 2 further includes an input 13 and an output 14 for a medicinal preparation in the aqueous state.

Figure 2:
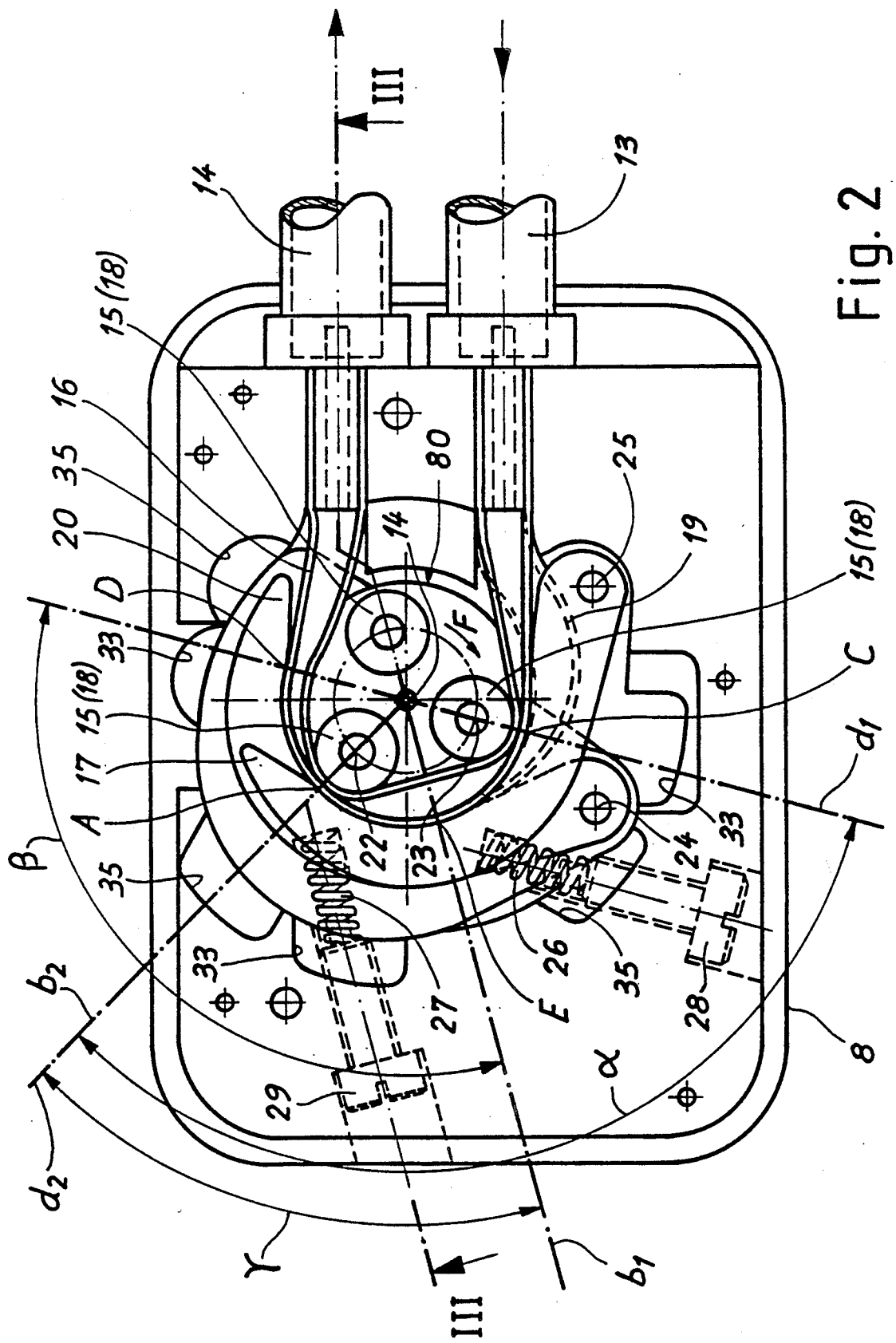
FIG. 2 is a plan view of a pump module, the cover and certain other parts having been removed in order to facilitate understanding thereof.
Figure 3:
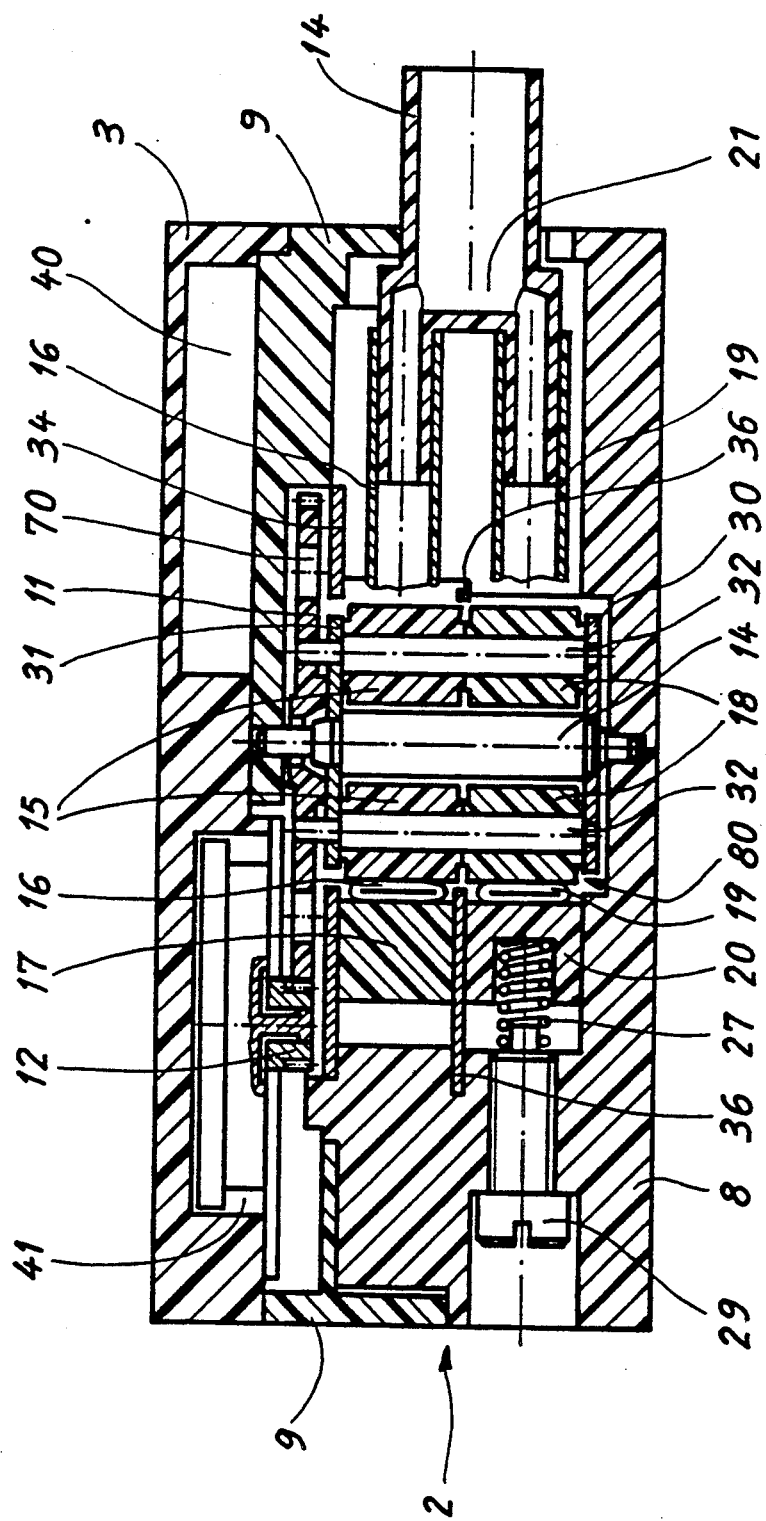
FIG. 3 is a cross-section of the pump according to the invention for which the pump module has been cut along line III—III of FIG. 2.

A preferred embodiment of the pump module will now be described having reference to FIGS. 2 and 3. This module is equipped with a rotor 80 borne on a shaft 14. Rotor 80 includes a first set of rollers 15 revolving along a first flexible pipe 16 and compressing it locally against a first backing 17. This first backing surrounds the first pipe along a first predetermined arc length AC. In an analogous manner, rotor 80 includes also a second set of rollers 18 revolving along a second flexible pipe 19 and locally compressing it against a second backing 20. This second backing surrounds the second pipe over a second arc of predetermined length DE. FIGS. 2 and 3 show that the rollers 15 and 18 are coaxially arranged two by two and that the arcs AC and DE exhibit substantially the same length. In the same manner it is seen on FIG. 3 that the outputs of pipes 16 and 19 are connected in parallel by means of a Y coupling 21 to end up at a common output 14 if the rotor turns in the sense of arrow F. It is the same for the common input 13, although the parallel connection does not show up on FIG. 3. FIG. 2 further shows that the first and second backings 17 and 20 are angularly offset in a manner such that the bisectors $b_1$ and $b_2$ of angles $\alpha$ and $\beta$ which they respectively subtend form between them an angle $\gamma$ which is half of the angle (for example the angle $\alpha$) formed by two straight lines $d_1$ and $d_2$ issuing from shaft 14 of the rotor and respectively cutting axes 22, 23 of two neighbouring rollers 15.

This arrangement enables regularizing the pump discharge as has been explained hereinabove with reference to document GB 1 595 901. In this respect it will be understood that if each set of rollers includes three rollers 15, respectively 18, equally distributed about the axis 40 of rotor 80, the backings 17 and 20 will be offset by an angle substantially equal to 60° which moreover is the case as shown on FIG. 2.

The backings supporting the pipes against the rotor may be obtained in various manners. In the embodiment of FIG. 2, backings 17 and 20 each exhibit the form of a hook pivoted at one of its ends, for instance around pins 24 and 25 respectively. Hooks 17 and 20 are pressed against pipes 16 and 19 respectively by means of springs 26 and 27 respectively, themselves held in place by screws 28, 29 threaded into the body of pump 8.

If one now refers to FIG. 3, it will be noticed that the rotor is formed of two end plates 30 and 31 between which are maintained the rollers 15 and 18 adapted to turn around axes 32. Here it will be noted that the rollers 15 are independent from rollers 18, which permits them to turn at different speeds. One benefits from the ends of axes 32 in order to fasten the gear 11 to rotor 80. FIG. 3 further shows that the first and second backings 17 and 20 are separated by a plate 36 which surrounds rotor 80 and which is arranged perpendicularly to shaft 14. This plate serves as a brace for the backings which thus gives them greater freedom of action. The plate also serves as a guide for each of pipes 16 and 19 which it maintains at the level of rollers 15 and 18 respectively. This plate is not drawn on FIG. 2 in order not to unduly overload said figure. There has however been referenced on FIG. 2 housings 33 in which plate 36 is supported. FIG. 3 further shows a second plate 34 located under gear 11 and which also serves as an upper guide for the flexible pipe 16. This second plate is not seen on FIG. 2 where, on the other hand, housings 35 are shown which serve as support points for plate 34.

The description of the pump module which has just been given is based on the employment of two flexible pipes placed in parallel and this for the reasons indicated. The invention however is not limited to a pump exhibiting two pipes and could exhibit one only or more than two.

An embodiment of the motor module will now be described having reference to FIGS. 1, 3 and 4. In accordance with the invention, the motor module includes a stepping motor driving a down gearing chain bearing at its end a power take-off shown by pinion 12 on FIG. 1. As has already been indicated, pinion 12 is adapted to drive gear 11 of the pump module when the two modules are assembled. According to the invention, the stepping motor is energized by energy pulses from a control circuit itself controlled by a frequency divider receiving a signal from a time base, such elements being energized from a DC source provided by a power cell. On FIG. 1, the motor module shows a housing 40 serving to accommodate the power cell and a housing 41 serving to accommodate the gearing, the motor, the control circuit, the frequency divider and the time base. An opening 42 serves to house a switch for turning on the system or putting it out of circuit. FIG. 3 which shows a cross-section of the completely assembled pump also shows the housings 40 and 41 as well as the power take-off or pinion 12 of the motor module engaged with the coupling element or gear 11 of the pump module.

Figure 4:
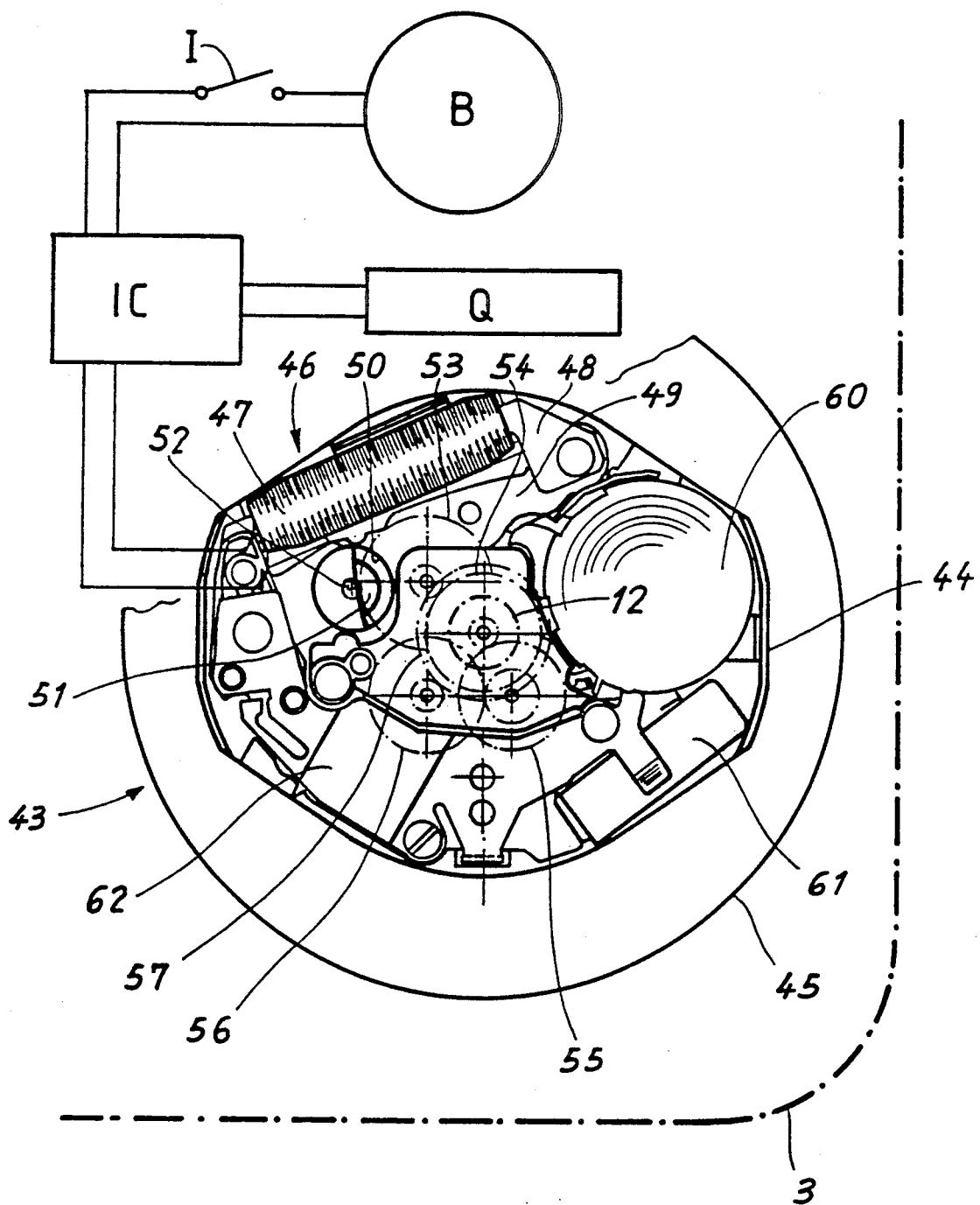
FIG. 4 is a partial plan view of the motor module of the pump.

FIG. 4 which is a partial view of the motor module of the pump shows in detail a driving mechanism 43 including a movement 44 fastened onto a plate 45, this latter being secured to the pump module 3. All of these elements find place in the housing 41 sketched on FIG. 1. The movement 44 includes a stepping motor 46, preferably of the type employed in a wristwatch and for which a description of the principle is given, for instance in the U.S. Pat. U.S. Application No. 2 909 685. FIG. 4 shows that the motor 46 includes a winding 47, a core 48 and a stator 49 exhibiting two poles separated by a circular opening 50 in which moves a diametrally magnetized rotor 51. On the rotor axis is found a pinion 52 which drives gearing including a kinematic chain of gear elements referenced in the order in which they appear in the chain by 53, 54, 55, 56 and 57. On the axis of gear element 57 will be found the power take-off or pinion 12 which has already been mentioned. Preferably the entire movement including the motor and the gearing is a timepiece movement such as employed for instance in a wristwatch. In this case the wheel set 54 is known as the seconds wheel and the wheel set 57 the hours wheel. In this special application the output pinion 12 replaces the hours hand.

As is further shown on FIG. 4, motor 46 is energized by a block IC comprising a control circuit, itself commanded by a frequency divider receiving the signal furnished by a time base Q. The time base will be preferably a quartz oscillator known for its great stability which provides the pump with a constant discharge. The block IC is commonly formed from a monoblock integrated circuit. A cell or battery B coupled to the system by a switch I provides the necessary energy. The control system for the operation of the motor is likewise known from the technology employed over a long period in wristwatches. One will find a description for instance in the U.S. Pat. U.S. Application No. 3 742 697.

FIG. 4 also shows that the movement 44 has had eliminated therefrom the cell, the quartz and the integrated circuit which are normally found at the places referenced 60, 61 and 62 respectively. In the embodiment taken as an example, it is preferred to place these elements outside the movement.

There will now be given an example of a practical embodiment of the invention. The stepping motor as chosen operates correctly up to a frequency of about 105 Hz. Starting with a standard timepiece quartz regulated at 32'768 Hz, one begins by dividing the frequency by means of six divide-by-two circuits, this giving a frequency of 512 Hz which is further divided once by a divide-by-five circuit, this resulting in a motor energizing frequency of 102.4 Hz. Since the motor as chosen is a bipolar single phase motor, its shaft will make two steps per revolution and will rotate at the speed of 51.2 revolutions per second. Between the shaft of the motor bearing pinion 52 and the shaft of the pump bearing gear 11, the reduction is 1:129'600, this giving a speed of rotation of the gear 11 of 1 revolution in 42 minutes 11 seconds. With this rotation speed, there has been measured an average discharge of 70 mm³ during the same time period. It is evident that the figures as given are an example of an embodiment and that the discharge may be modified by varying the quartz frequency, the number of divider stages, the reduction ratio given by the gear train and/or finally, the type of motor employed.

Figure 5:
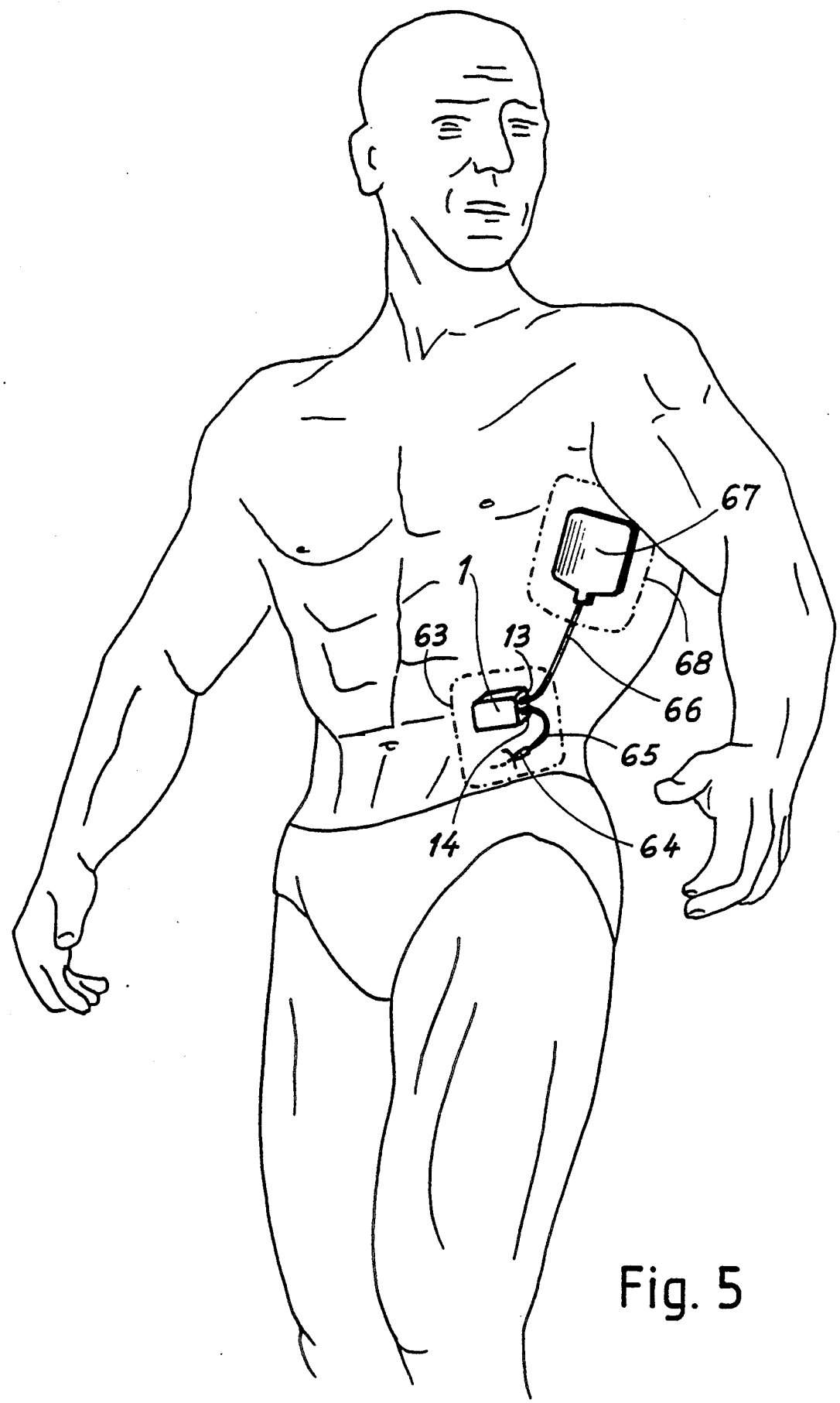
FIG. 5 shows how the miniature peristaltic pump according to the invention may be carried on the human body.

The peristaltic pump according to the invention has as main characteristic that of being of very small dimensions such that it may be worn or carried directly on the body as shown on FIG. 5. Here the pump 1 is placed on the abdomen of the body and is held there by means of an adhesive 63. The output 14 of the pump is coupled to a hypodermic needle 64 by a tube 65. The input 13 of the pump is coupled by means of a tube 66 to a reservoir 67 containing the medicinal preparation. The reservoir, placed in the region of the armpit, is held on the body by means of another adhesive 68.

It has been seen hereinabove that the discharge of the pump according to the invention gives out a small liquid discharge which is a condition for its miniaturization. It is thus intended to cure illnesses other than diabetes for which stronger discharges are necessary at certain times of day. It is not in principle intended to deliver variable discharges over the course of time, such discharge however could be interrupted if necessary during certain periods thanks to the built-in switch. If the performances of the pump are limited, such pump may however be employed in numerous cases for which it will be appreciated for its smallness and its autonomy. It will be also appreciated for its very low price since it comprises only inexpensive components and may be manufactured in large quantities, particularly for the part formed by the motor module. Accordingly the pump may be thrown away after use.

It is likewise important that the pump be formed of two separable modules. It is known in effect that it is necessary to sterilize the pump before employment, which may be effected by gamma rays. The pump module which bears no electrical element and is formed almost entirely of plastics material, is well adapted to this type of sterilization. On the other hand the motor module will not withstand such treatment (motor, integrated circuit, etc.). Furthermore, if the modules are separable, it is understood that with a single pump module one may employ different motor modules differing above all in respect of the speed of rotation of the power take-off according to the volume of liquid to be injected.

It has been explained hereinabove that the pump of the invention generally exhibits a very small discharge and it will be understood that the speed of rotation of gear 11 is so low that it does not enable priming of the pump. To enable this operation, gear 11 includes a series of holes 70 (see FIGS. 1 and 3) which are rendered accessible to the practitioner before the motor module is coupled to the pump module. By employing the tip of a ballpoint pen for instance, the practitioner may turn gear 11 at a speed enabling priming of the pump.

It is further mentioned that the pump may be sealed against dust, natural secretions of the body and water thanks to the coating means enveloping the entire pump. However, in place of coating one could by means of constructions and by means of seals assure sealing of the pump body 8 relative to the cover 9 and the sealing of the pump module 2 relative to the motor module 3. In this latter case one will likewise seal all openings such as the input and output 13 and 14, zone 42 where switch I is located, and in general all passage holes (screws etc.).

It has been mentioned hereinabove that at least the pump module is formed of plastics material. In a general manner there will be chosen a material for both modules which is insensible to attacks by natural secretions of the human body.

What we claim:

1. A minature peristaltic pump especially adapted to be carried on the human body for slow and continuous injection of medicinal preparations in the aqueous state, including a pump having a rotor borne on a shaft around which are evenly distributed rollers given a rovolving movement rolling along at least one flexible tube so as to compress it against at least one backing which surrounds said tube over a predetermined length of arc so as to permit the sucking in and the expelling of said medicinal preparation, said shaft being provided with a coupling element, a stepping motor driving a down gearing chain bearing at its end a power take-off, a control circuit for providing the motor with energizing pulses coming from a time base followed by a frequency divider and a power cell, said minature peristaltic pump being characterized in that it comprises a separable pump module and a separable motor module, said modules being adapted to be assembled with, and after assembly separated from, one another, the pump module comprising the pump itself provided with its coupling element and the motor module comprising the stepping motor, the down gearing chain provided with its power take-off, the control circuit, the frequency divider and the power cell, said coupling element being engaged with said power take-off when said modules are assembled and being disengaged when said modules are separated after assembly, whereby said motor module and said pump module can be separated after assembly for purposes including sterilization of said pump module apart from said motor module and coupling of said pump module to another motor module.

2. A peristaltic pump as set forth in claim 1 wherein the time base comprises a quartz oscillator.

3. A peristaltic pump as set forth in claim 1 wherein at least the pump module is accommodated in a case formed of plastics material.

4. A peristaltic pump as set forth in claim 1 wherein the stepping motor and the down gearing chain form a movement of the type utilized for driving the hands in a wrist watch.

5. A peristaltic pump as set forth in claim 1 wherein the coupling element is a toothed wheel and the power takeoff is a toothed pinion.

6. A peristaltic pump as set forth in claim 5 wherein the toothed wheel is pierced with a plurality of holes accessible to the medical practitioner when the motor module is separated from the pump module so as to permit priming of the pump.

7. A peristaltic pump as set forth in claim 1 wherein the pump module includes first and second flexible tubes, the inputs and the outputs of which are respectively connected in parallel and wherein the rotor includes a double set of rollers coaxially arranged two-by-two, the first set rolling along the first flexible tube and locally compressing it against a first surrounding backing over a first predetermined length of arc and the second set rolling along the second flexible tube and locally compressing it against a second surrounding backing over a second predetermined length of arc, said first and second arcs having substantially the same length, said first and second backings being angularly offset in a manner such that the bisectors $b_1, b_2$ of the angles $\alpha, \beta$ which they subtend form between them an angle $\gamma$ equal to half the angle formed by two straight lines $d_1, d_2$ issuing from the rotor shaft and cutting respectively the axes of two neighbouring rollers of a same set.

8. A peristaltic pump as set forth in claim 7 wherein each set of rollers includes three rollers evenly distributed around the rotor shaft and wherein the first and second backings are offset by an angle $\gamma$ substantially equal to 60°.

9. A peristaltic pump as set forth in claim 7 wherein the first and second backings each have the form of a hook pivoted at one of its ends, said hook being pressed against the corresponding tube by means of a spring.

10. A peristaltic pump as set forth in claim 7 wherein the first and second backings are separated by a plate surrounding the rotor and arranged perpendicular to its shaft, said plate serving at the same time as a brace for said backings and as a guide for said first and second tubes so as to maintain each tube at the level of the corresponding set of rollers.

* * * * *